(12) United States Patent
Isacsson et al.

(10) Patent No.: US 7,771,339 B2
(45) Date of Patent: Aug. 10, 2010

(54) METHOD AND SYSTEM FOR RADIOTHERAPY TREATMENT

(75) Inventors: Ulf Isacsson, Uppsala (SE); Kristina Nilsson, Uppsala (SE); Stefan Asplund, Jaerlassa (SE)

(73) Assignee: AB Mimator, Uppsala (SE)

( * ) Notice: Subject to any disclaimer, the term of this patent is extended or adjusted under 35 U.S.C. 154(b) by 304 days.

(21) Appl. No.: 11/807,951

(22) Filed: May 30, 2007

(65) Prior Publication Data

US 2007/0284545 A1    Dec. 13, 2007

Related U.S. Application Data

(60) Provisional application No. 60/809,616, filed on May 31, 2006.

(51) Int. Cl.
*A61N 5/00* (2006.01)
(52) U.S. Cl. .............. 600/1; 600/2; 600/3; 600/6; 600/9; 128/898; 378/65; 250/491.1; 250/492.1; 250/493.1
(58) Field of Classification Search .......... 250/493.1, 250/492.1, 491.1; 378/65; 600/101, 102, 600/427, 1–9; 128/898
See application file for complete search history.

(56) References Cited

U.S. PATENT DOCUMENTS

| | | | |
|---|---|---|---|
| 3,555,276 A | | 1/1971 | Helm et al |
| 3,612,509 A | * | 10/1971 | Boston et al. .................. 269/98 |
| 3,845,945 A | | 11/1974 | Lawley et al |
| 3,889,676 A | * | 6/1975 | Greene .................. 604/101.05 |
| 4,294,264 A | * | 10/1981 | Fischell et al. .............. 600/591 |
| 4,311,154 A | * | 1/1982 | Sterzer et al. ............... 607/102 |
| 4,554,909 A | * | 11/1985 | Pino y Torres ................. 600/6 |

(Continued)

FOREIGN PATENT DOCUMENTS

DE    3823604    1/1990

(Continued)

OTHER PUBLICATIONS

Ahnesjö et al, "A Pencil Beam Model for Photon Dose Calculation," *Med. Phys.*, 19 (2), Mar./Apr. 1992, pp. 263-273.

(Continued)

*Primary Examiner*—Robert Kim
*Assistant Examiner*—Michael J Logie
(74) *Attorney, Agent, or Firm*—Porter Wright Morris & Arthur

(57) ABSTRACT

A method for radiotherapy treatment of a target organ in the vicinity of the rectum in an individual comprises withdrawing the rectum in a dorsal direction to increase a distance between the rectum and the target organ, and administering a therapeutical dose of radiation to the target organ while the rectum is in the withdrawn position. In one embodiment, the target organ is the prostate. A system for use in radiotherapy treatment of a target organ in the vicinity of the rectum in an individual comprises a cylindrical rectal rod adapted for insertion into a rectum of the individual, and a support surface operable to support an individual in a lithotomy position to receive a beam of radiation to the target organ. The system may further include a radiation source for administering a beam of radiation to the target organ of an individual.

25 Claims, 6 Drawing Sheets

U.S. PATENT DOCUMENTS

| | | | | |
|---|---|---|---|---|
| 4,637,814 | A * | 1/1987 | Leiboff | 604/27 |
| 4,638,806 | A * | 1/1987 | Bartlett | 607/105 |
| 4,817,616 | A * | 4/1989 | Goldstein | 600/463 |
| 5,234,004 | A * | 8/1993 | Hascoet et al. | 607/116 |
| 5,474,071 | A * | 12/1995 | Chapelon et al. | 600/439 |
| 5,562,594 | A * | 10/1996 | Weeks | 600/3 |
| 5,613,254 | A | 3/1997 | Clayman et al. | |
| 5,961,527 | A * | 10/1999 | Whitmore et al. | 606/130 |
| 6,064,914 | A * | 5/2000 | Trachtenberg | 607/102 |
| 6,106,517 | A * | 8/2000 | Zupkas | 606/20 |
| 6,179,785 | B1* | 1/2001 | Martinosky et al. | 600/549 |
| 6,235,037 | B1* | 5/2001 | East et al. | 606/119 |
| 6,390,968 | B1* | 5/2002 | Harmon | 600/6 |
| 6,394,965 | B1* | 5/2002 | Klein | 600/564 |
| 6,561,966 | B1* | 5/2003 | Smith et al. | 600/3 |
| RE38,143 | E * | 6/2003 | Tierney et al. | 607/101 |
| 6,698,431 | B1* | 3/2004 | Harris et al. | 128/845 |
| 6,699,171 | B2* | 3/2004 | Harmon | 600/6 |
| 6,746,465 | B2* | 6/2004 | Diederich et al. | 606/192 |
| 6,824,516 | B2* | 11/2004 | Batten et al. | 600/439 |
| 7,438,685 | B2* | 10/2008 | Burdette et al. | 600/439 |
| 2001/0047134 | A1* | 11/2001 | Holdaway et al. | 600/459 |
| 2002/0010502 | A1* | 1/2002 | Trachtenberg | 607/102 |
| 2002/0016540 | A1* | 2/2002 | Mikus et al. | 600/407 |
| 2002/0038117 | A1* | 3/2002 | Tokita et al. | 606/1 |
| 2003/0112922 | A1* | 6/2003 | Burdette et al. | 378/65 |
| 2003/0153803 | A1* | 8/2003 | Harmon | 600/6 |
| 2003/0233123 | A1* | 12/2003 | Kindlein et al. | 607/2 |
| 2004/0073107 | A1* | 4/2004 | Sioshansi et al. | 600/431 |
| 2004/0094162 | A1* | 5/2004 | Noyes | 128/843 |
| 2005/0038488 | A1* | 2/2005 | Jaafar et al. | 607/100 |
| 2005/0070961 | A1* | 3/2005 | Maki et al. | 607/2 |
| 2005/0166325 | A1 | 8/2005 | Tidwell | |
| 2006/0004251 | A1* | 1/2006 | Bookwalter et al. | 600/38 |
| 2006/0074303 | A1* | 4/2006 | Chornenky et al. | 600/427 |
| 2006/0100475 | A1* | 5/2006 | White et al. | 600/3 |
| 2006/0122538 | A1* | 6/2006 | Kellett et al. | 600/587 |
| 2006/0173235 | A1* | 8/2006 | Lim et al. | 600/6 |
| 2006/0224034 | A1* | 10/2006 | Reever | 600/3 |
| 2006/0241368 | A1* | 10/2006 | Fichtinger et al. | 600/407 |
| 2006/0258933 | A1* | 11/2006 | Ellis et al. | 600/407 |
| 2007/0083080 | A1* | 4/2007 | Kim | 600/102 |
| 2008/0033471 | A1* | 2/2008 | Paz et al. | 606/190 |

FOREIGN PATENT DOCUMENTS

| | | |
|---|---|---|
| LU | 82294 | 7/1980 |
| WO | 9831273 | 7/1998 |

OTHER PUBLICATIONS

Åström et al, "Long-Term Outcome of High Dose Rate Brachytherapy in Radiotherapy of Localised Prostate Cancer," *Radiotherapy & Oncology*, 74 (2005) pp. 157-161.

Mangar et al, "Technological Advances in Radiotherapy for the Treatment of Localised Prostate Cancer," *European Journal of Cancer*, 41 (2005) pp. 908-921.

Mechalakos et al, "Time Trends in Organ Position and Volume in Patients Receiving Prostate Three-Dimensional Conformal Radiotherapy," *Radiotherapy & Oncology*, 62 (2002) pp. 261-265.

Mock et al, "Comparative Treatment Planning on Localized Prostate Carcinoma," *Strahlenther Onkol*, 2005 No. 7, pp. 448-455.

Russell et al, "Implementation of Pencil Kernel and Depth Penetration Algorithms for Treatment Planning of Proton Beams," *Phys. Med. Biol.*, 45 (2000) pp. 9-27.

Holupka et al, "Ultrasound Image Fusion for External Beam Radiotherapy for Prostate Cancer," *Int. J. Radiation Oncology Biol. Phys.*, vol. 35, No. 5, 1996, pp. 975-984.

Jung et al, "The Conceptual Design of a Radiation Oncology Planning System," *Computer Methods and Programs in Biomedicine*, 52 (1997) pp. 79-92.

Montelius et al, "Quality Assurance Tests of the TMS-Radix Treatment Planning System," *Advanced Radiation Therapy Tumor Response Monitoring and Treatment Planning*, Breit, Editior-In-Chief, Springer-Verlag, Berlin, 1992, pp. 523-527.

\* cited by examiner

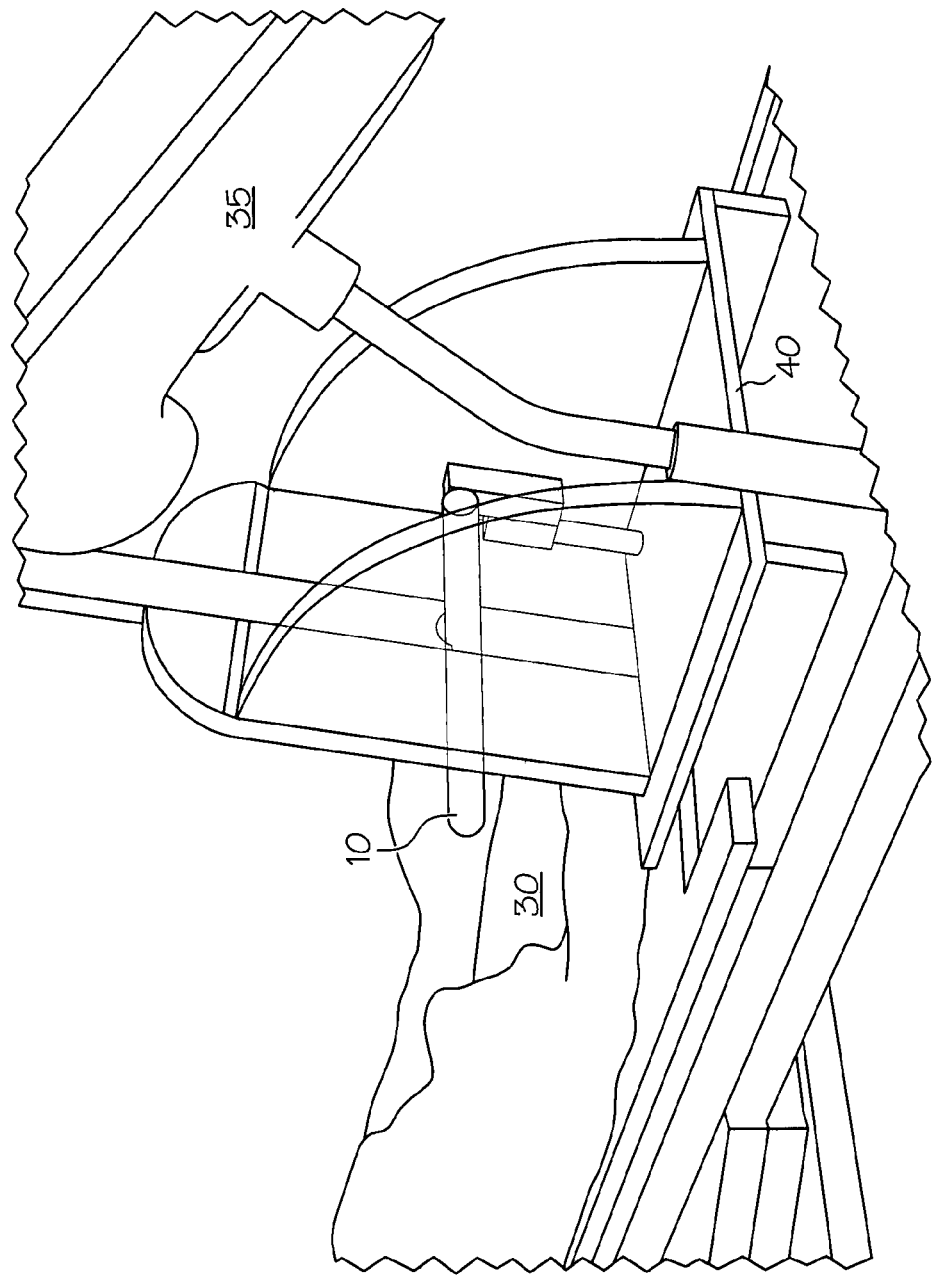

METHOD AND SYSTEM FOR RADIOTHERAPY TREATMENT

RELATED APPLICATION

This application claims the benefit under 35 U.S.C. §119 of U.S. Application Ser. No. 60/809,616 filed May 31, 2006.

FIELD OF THE INVENTION

The present invention is directed to methods and systems for radiotherapy treatment of a target organ in the vicinity of the rectum in an individual, for example for treatment of prostate cancer, cervical cancer, uterine cancer or the like, and more specifically, the present invention is directed to such methods and systems wherein the rectum is withdrawn in a dorsal direction to reduce radiation administration to non-target areas, and particularly to reduce radiation administration to the rectum.

BACKGROUND OF THE INVENTION

External beam radiotherapy (EBRT) is widely accepted as a curative treatment modality for localized prostate cancer. See, for example, Holupka et al, "Ultrasound image fusion for external beam radiotherapy for prostate cancer," *Int. J Oncology Biol. Phys.*, 1996:35:975-84. However, in order to cure localized cancer of the prostate with radiotherapy, a high dose is needed. Different escalation schedules are used world wide. Generally, it is desirable to decrease the target volume while employing high radiation doses and to use markers in the prostate to increase the positioning accuracy of the target volume. There are, however, radiation dose limitations that should be followed in order to avoid complications in dose sensitive organs, including, but not limited to, the rectum, the bladder and the hips.

Another approach for treatment of prostate cancer is the use of low dose rate brachytherapy, seeds, or 3D conformal radiotherapy combined with a boost of high dose rate (HDR) brachytherapy. See, for example, Åström et al, "Long-term outcome of high dose rate brachytherapy in radiotherapy of localized prostate cancer," *Radiother. Oncol.*, 2005:74:157-61. Intensity Modulated Radiotherapy (IMRT) has improved the conformality of the treatment delivery and improved clinical outcomes with regard to the delivery of external beam radiotherapy, as described by Mangar et al, "Technological advances in radiotherapy for the treatment of localized prostate cancer," *Eur. J Cancer*, 2005:41:908-21.

Proton treatment of the prostate is also employed, either as a single treatment modality or in combination with conventional radiotherapy. Mock et al, "Comparative treatment planning on localized prostate carcinoma conformal photon-versus proton-based radiotherapy," *Strahlenther Onkol.*, 2005: 181:448-55, have reported that the advantageous dose distribution of proton beam radiotherapy for prostate cancer may result in reduced side effects compared to IMRT. With a single perineal proton beam, it is possible to reduce the volume of the rectal wall included in the high dose region as compared with conventional X-ray radiotherapy, Benk et al, "Late rectal bleeding following combined X-ray and proton high dose irradiation for patients with stages T3-T4 prostate carcinoma," *Int. J Radiat. Oncol. Biol. Phys.*, 1993:26:551-7.

One conventional radiotherapy treatment of localized prostate cancer employs a combination of 3D conformal radiotherapy, with either HDR brachytherapy or a proton boost. The external photon treatment is given in 25 2 Gy fractions, the brachytherapy with two 10 Gy fractions and the proton beam treatment with four 5 Gy fractions. The proton treatment is given with high precision, using gold markers, and the dose to rectum is typically considerably less as compared with EBRT techniques. The rectal toxicity is similar to the combination treatment with EBRT and HDR brachytherapy. The close relationship between the prostate and rectum, however, typically demands a compromise between dose to target and organ at risk. The positioning of the prostate during radiotherapy is also important, since the prostate is known to move in the transversal or craniocaudal direction. Additionally, an internal rotation and tilt angle sometimes occurs which cannot be corrected, even by use of markers in the prostate.

High-precision radiotherapy techniques enable the delivery of dose distributions of increasing conformality relative to the target volume and surrounding critical tissues. In turn, such treatments have become increasingly sensitive to setup error and organ motion, as described by Mechalakos et al, "Time trends in organ position and volume in patients receiving prostate three-dimensional conformal radiotherapy," *Radiother Oncol.*, 2002:62:261-5. Often, however, treatment of prostate cancer with high-dose radiotherapies is not sufficient due to the close relationship between other organs, and specifically, the rectal wall and the prostate. Thus, a need exists for improved methods and systems for treatment of prostate cancer and for treatment in general of target areas in the vicinity of the rectum.

SUMMARY OF THE INVENTION

Accordingly, it is an object of the present invention to provide improved methods and systems for treatment of organs in the vicinity of the rectum, and, in one specific embodiment, for treatment of prostate cancer.

In one embodiment, the invention is directed to a method for radiotherapy treatment of a target organ in the vicinity of the rectum in an individual. The method comprises withdrawing the rectum in a dorsal direction to increase a distance between the rectum and the target organ, and administering a therapeutical dose of radiation to the target organ while the rectum is in the withdrawn position.

In another embodiment, the invention is directed to a system for use in radiotherapy treatment of a target organ in the vicinity of the rectum in an individual. The system comprises a cylindrical rectal rod adapted for insertion into a rectum of the individual, and a support surface operable to support an individual in a lithotomy position to receive a beam of radiation to the target organ. The system may further comprise a radiation source for administering a beam of radiation to the target organ, or may be used in combination with a pre-existing radiation source. In a further embodiment, the cylindrical rectal rod is adapted for insertion into a rectum of the individual in a direction parallel with a beam of radiation to be administered, while in other embodiments, orthogonal beam directions may be employed in the system.

The methods and systems of the present invention are advantageous in reducing radiation administration to areas other than the target organ, particularly in reducing radiation administration to the rectum. The methods and systems may also be advantageous for maintaining the target organ in position during radiation administration. This and additional embodiments and advantages of the present invention may be more fully apparent in view of the following detailed description.

BRIEF DESCRIPTION OF THE DRAWINGS

The following detailed description will be more fully understood in view of the drawing in which:

FIG. 2 shows one embodiment of a system according to the present invention; and

Figure 1:
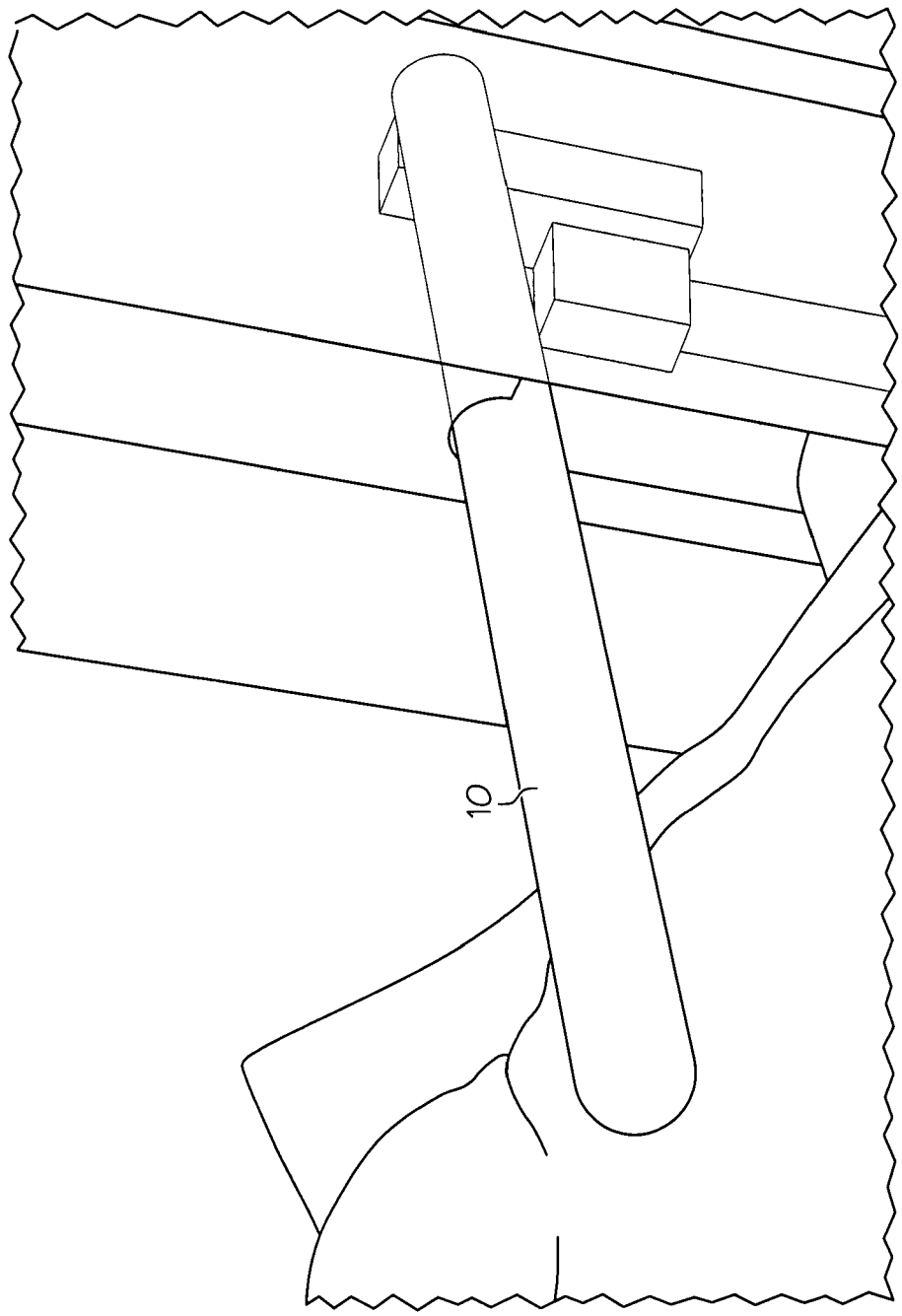
FIG. 1 shows one embodiment of a rectal rod for use in the present methods and systems.
Figure 3A:
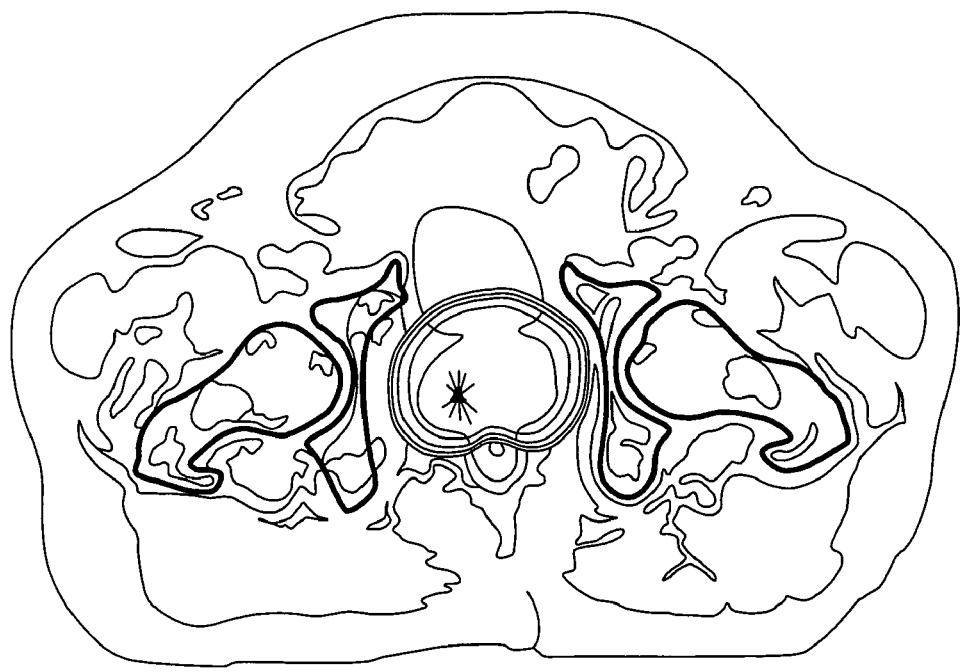
FIG. 3a-3d show dose distributions in a transverse and in a sagital section in the central part of a prostate of an individual in accordance with a method of the invention as described in the Example (FIGS. 3c and 3d) and in accordance with a similar method not employing a rectal rod (FIGS. 3a and 3b).
Figure 3B:
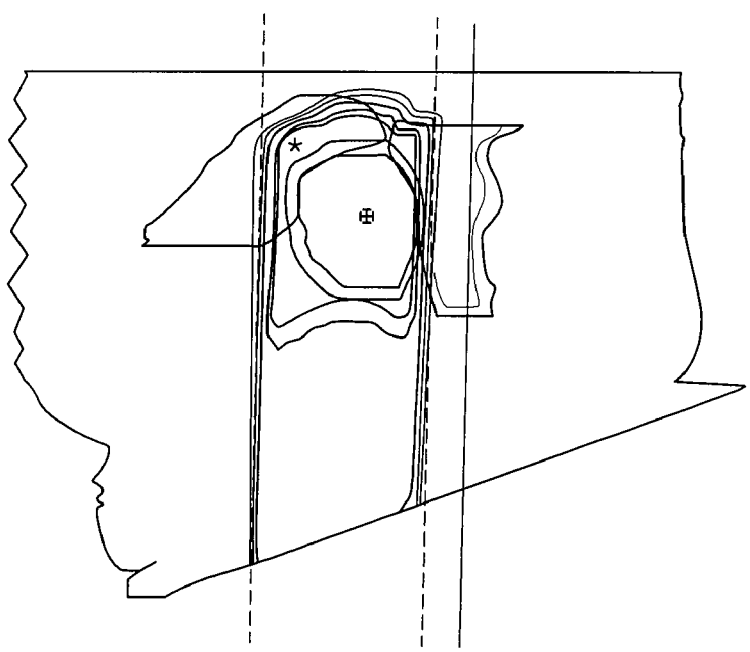
Figure 3C:
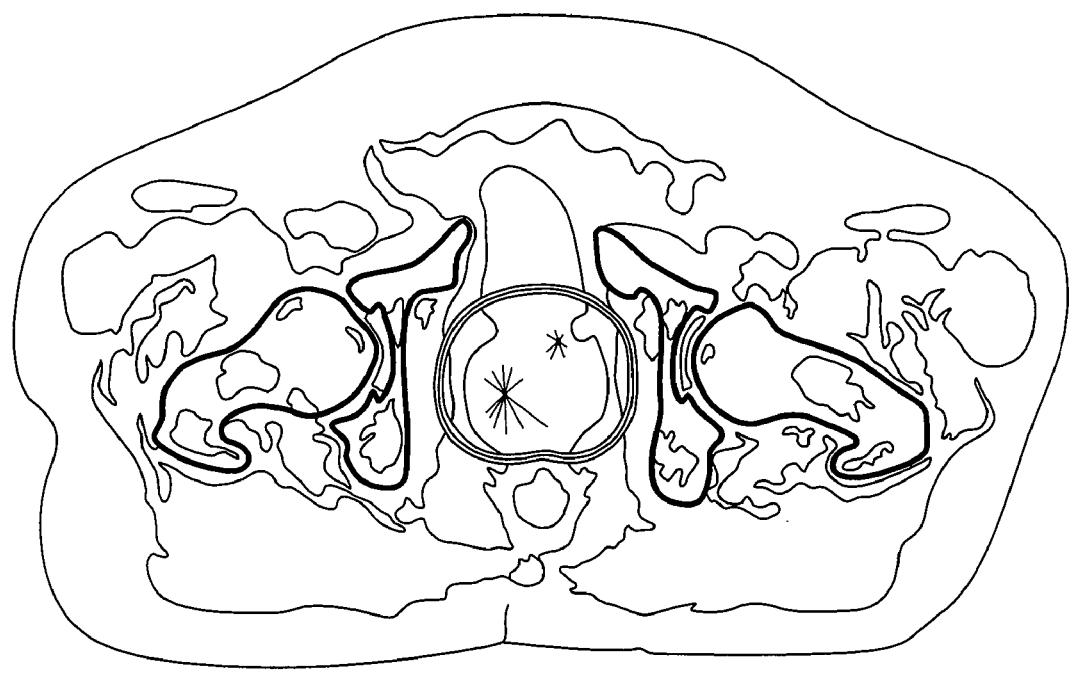
Figure 3D:
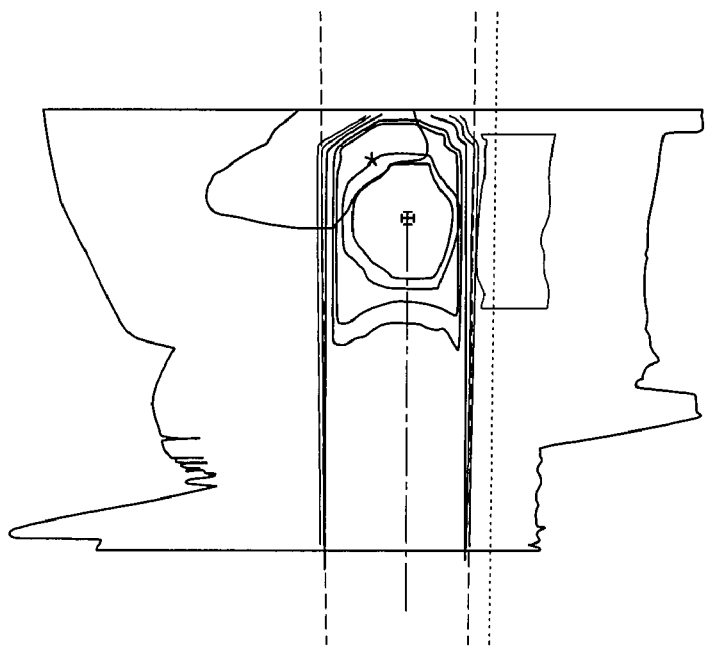

The embodiments set forth in the drawing are illustrative in nature and are not intended to be limiting of the invention defined by the claims. Moreover, individual features of the drawing and the invention will be more fully apparent and understood in view of the detailed description.

DETAILED DESCRIPTION

The present invention is directed to methods and systems for radiotherapy treatment of a target organ in the vicinity of the rectum in an individual. In one embodiment, the target organ is the prostate and the methods and systems are for treatment of prostate cancer. In additional embodiments, the target organ may be the vagina, the cervix, the uterus, or other organs, and the methods and systems are for treatment of one or more conditions thereof. While the present detailed description may specifically refer to treatment of prostate cancer, it must be appreciated that the inventive methods and systems may be employed as described for treatment of other conditions in any organ in the vicinity of the rectum. Further, the methods and systems may be used for various forms of radiotherapy treatment as desired. In a specific embodiment, the radiotherapy is proton beam radiotherapy, but the present methods and systems may apply equally well and provide improvements for use with other radiotherapies as well or other therapies where an increased distance between a target organ and the rectum is desired.

In accordance with the present invention, the method comprises withdrawing the rectum in a dorsal direction to increase a distance between the rectum and the target organ, such as the prostate, and administering a therapeutical dose of radiation to the target organ while the rectum is in the withdrawn position. It has been discovered that withdrawal of the rectum as described can significantly reduce the rectal volume receiving high doses of radiation and therefore can significantly reduce adverse side effects to the rectum as compared with various conventional radiation therapies. In a specific embodiment, the rectum is withdrawn by insertion of a cylindrically shaped rectal rod into the rectum and withdrawal of the rectum therewith. In addition, the rectal rod can be positioned to maintain the target organ such as the prostate in position during radiotherapy, thereby preventing movement in a transversal or craniocaudal direction, and preferably also preventing internal rotation and/or tilting of the prostate or other target organ during radiotherapy.

FIG. 1 shows one embodiment of such a rectal rod. As described, the rod 10 is cylindrically shaped and is sized and otherwise configured to withdraw the rectum in a dorsal direction upon insertion and to extend to a position operable to maintain the prostate in a single position as described. The rectal rod may be formed of any suitable material and in one embodiment is formed of polymethylmethacrylate, available commercially as Perspex®. In one embodiment, the rod is from about 20 cm to about 30 cm in length and from about 1 cm to about 3 cm in diameter.

In one embodiment of the present methods, the rod is positioned such that the rod and a beam of the administered radiation are substantially parallel. A system according to the invention may be employed to conveniently practice the present methods. Such a system is shown in FIG. 2 and comprises the described cylindrical rectal rod 10 adapted for insertion into the rectum of the individual in a direction parallel with a beam of radiation to be administered, and a support surface 30 operable to support an individual in a lithotomy position to receive a beam of radiation to the target organ. In one embodiment, the support surface 30 comprises a fixation couch, and preferably includes a support 35 for an individual's legs as described in further detail in the Example. Further, the system may include a perineum plate 40 operable to standardize a distance from the skin to the target organ, for example the prostate, of an individual, in order to standardize treatments as also described in further detail in the Example.

According to specific embodiments of the present method, a combination of radiation therapies may be employed. For example, in one embodiment, X-ray treatment may be administered before, during or subsequent to proton beam therapy. In a more specific embodiment, an individual is treated with proton beam followed by X-ray therapy. As will be apparent to one of ordinary skill in the art, one or more of the radiation therapies may be administered in successive doses.

In one embodiment of the invention, at least one detectable marker is applied to the target organ such as the prostate to allow detection of the target organ position during administration of radiation. Various markers are known in the art and are suitable for use in the present methods. For example, gold markers may be employed and located by insertion in the prostate using a needle. In a specific embodiment, at least three markers are applied to the target organ to provide a three-dimensional localization of the target organ position, for example the prostate position, from real-time portal images during administration of radiation. In a further embodiment, at least four markers are employed.

As described in the Example, the present methods can advantageously reduce the volume of non-target organ tissue, for example, non-prostate tissue, and particularly the rectal volume, receiving high doses of radiation. In a specific embodiment of the present methods, the radiation comprises proton beam radiation or a combination of X-ray and proton beam radiation and the rectal volume receiving 70 Gy or more of radiation is less than about 10 ml, more specifically less than about 5 ml. In a further embodiment, the radiation comprises proton beam radiation or a combination of X-ray and proton beam radiation and the rectal volume receiving 70 Gy or more of radiation is at least 50% less, more specifically at least 70% less, than the rectal volume receiving 70 Gy or more of radiation in a similar method wherein the rectum is not withdrawn.

Figure 4:
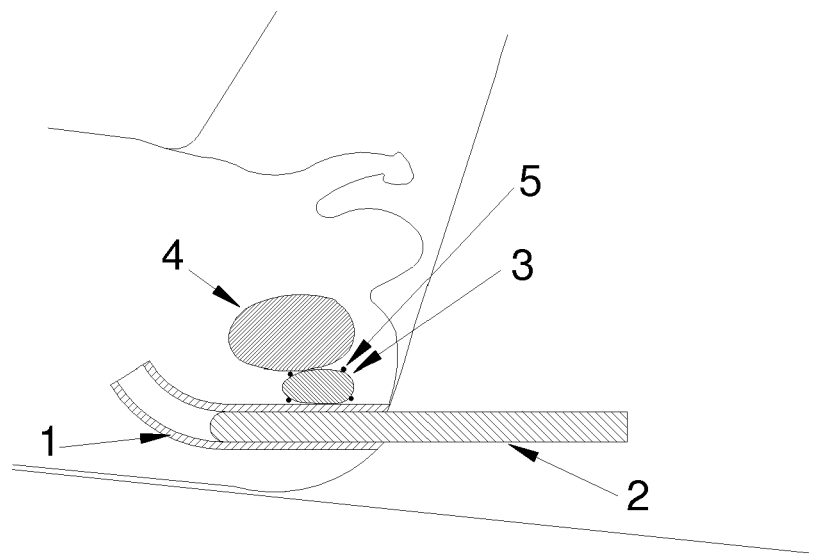
FIG. 4 is a schematic drawing of a sagittal section of a patient showing the insertion of a rectal rod in the rectum, prior to withdrawing the rectum in a dorsal direction.
Figure 5:
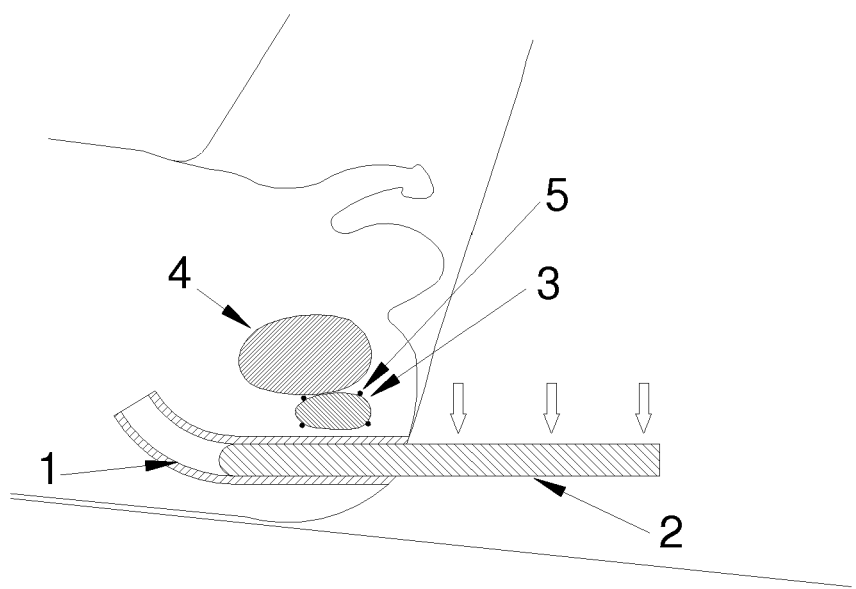
FIG. 5 is a schematic drawing of a sagittal section of a patient showing the rectum withdrawn from the prostate in a dorsal direction.
Figure 6:
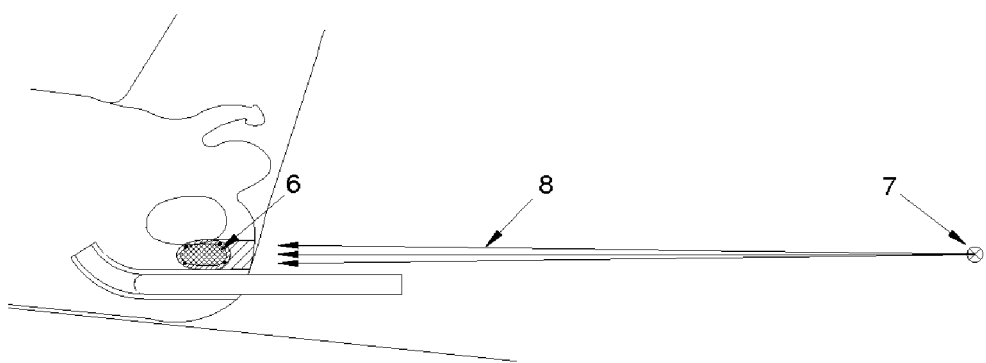
FIG. 6 is a schematic drawing of a sagittal section of a patient showing radiation administered in a direction substantially parallel with the rectal rod.

Attention is directed to FIGS. 4-6 which schematically illustrate one embodiment of the methods and systems of the invention. As shown in FIG. 4, a rectal rod 2 is inserted into a patient's rectum 1, shown proximate the prostate 3, shown proximate to the bladder 4. As shown in FIG. 5, the rectal rod 2 is then moved in a dorsal direction, shown by the arrows in FIG. 5, to withdraw the rectum in a dorsal direction and thereby increase the distance between the rectum and the target organ, i.e., the prostate. Detectable markers 5 are placed at the prostate to better target administered radiation. As shown in FIG. 6, radiation is delivered to the target organ at reference number 6, from a radiation source 7. In this embodiment, the radiation is directed parallel, as shown by reference number 8, with the rectal rod 2. In FIG. 6, the more dense crosshatching indicates the area of therapeutical dose to the target organ and a margin area, while the less dense crosshatching indicates an area receiving a lower dose of radiation, i.e., healthy tissue.

The following Example describes methods and systems according to the invention and shows improvement provided by the inventive methods as compared with a similar method in which the rectum is not withdrawn.

EXAMPLE

Ten patients with proven biopsy and localized adenocarcinoma of the prostate are included in the present study. The patients receive 4 gold markers in the prostate, inserted with needles through the perineum. The gold markers are spread out in the prostate to ensure a satisfying 3D positioning. The ten patients are treated with proton beam therapy of 20 Gy given in four fractions to the prostate alone followed by X-ray therapy to a prescribed dose of 50 Gy in 2 Gy fractions five days per week to the entire prostate, including the seminal vesicles.

For the proton beam therapy, the patients are immobilized with a specially constructed fixation couch on which a custom-shaped vacuum pillow is placed for individual fixation. The couch also contains support for the legs and a Lucite® (polymethylmethacrylate) plate in the perineum for standardizing the distance from the skin to the prostate. The patients are positioned in lithotomy position and the couch allows the patients to be tilted in the cranial-caudal direction to closely match the horizontal proton beam with the rectal wall, i.e. the rectal wall and the proton beam should be parallel. To displace the rectal wall posteriorly, a Lucite rectal rod is inserted during the preparation (fixation, CT and simulation) and the proton beam radiotherapy treatment. The rod is advanced posteriorly to maximize the separation between the prostate gland and the rectal wall. The rod is placed in a horizontal level, by aid of a water level, parallel with the proton beam, and the rectum is advanced posteriorly, the same distance every time. The patients are prescribed a laxative every day before fixation and gas was removed from the rectum by continuous suction.

Each day of the proton treatment, the patient is positioned in the same manner, confirmed with X-rays, anterior-posterior and lateral. The gold markers in the prostate and markers in the fixation device (including the rod inserted in rectum) are visible on the X-ray films. To have the patient optimally positioned (less than 1 mm) the same method, that Grusell and co-workers (1994) have described for intracranial treatments, is used (Grusell et al, "Patient positioning for fractionated precision radiation treatment of targets in the head using fiducial markers" *Radiother. Oncol.* (1994) 33:68-72. The Grusell et al positioning method determines the target position by X-ray imaging of markers that are placed in the patient's skull. In this study, the gold markers are placed within the target organ. During the X-ray treatment the patients are fixated in a conventional supine position and portal images were taken to verify the position. Each patient is CT scanned in the above described treatment position over the pelvic region with slice thickness of 2 mm. The CT images are obtained from a Siemens Sensation 16 scanner.

The clinical target volume (CTV) for the proton boost is the prostate. All patients undergo a diagnostic MRI study before radiotherapy. To define the planning target volume (PTV), a margin of 5 mm is applied around the CTV in all directions except dorsally, where 2 mm is used. The organ at risk is predominantly the rectum. The rectum is defined in two ways, first, the outer rectal wall (Rectum_out) and, second, the rectal mucosa (Rectum_in) and in both cases with the entire contents. Also, the bladder may be taken into consideration during treatment planning.

The image data is introduced into Helax-TMS™ (Treatment Management System, MDS Nordion Therapy System, Uppsala, Sweden) as described by Jung et al, "The conceptual design of a radiation oncology planning system," *Comput. Methods and Programs Biomed.*, 52:79-92 (1997). The system is provided with absorbed dose calculation algorithms for the different radiation modalities employed and has been subjected to adequate quality assurance tests (Montelius et al, "Quality assurance tests of the TMS-radix treatment planning system" in "Advanced radiation therapy tumour response monitoring and treatment planning," Breit, ed, Berlin, Heidelberg: Springer-Verlag, 1992, pp 523-7; Russell et al, "Implementation of pencil kernel and depth penetration algorithms for treatment planning of proton beams," *Phys. Med. Biol.*, 2000:45:9-27). Dose distributions are presented as isodose contours in the CT slices and as dose volume histograms (DVH), which represent the distribution of dose in selected volumes of interest. The dose distributions for X-rays and protons are calculated using a particle specific pencil beam algorithm (Ahnesjö et al, "A pencil beam model for photon dose calculation," *Med. Phys.*, 1992:19:263-73; Helax A B, "Dose Formalism and Models in Helax-TMS," Uppsala, Sweden, 1998; and Russell et al, 2000). The X-ray treatment is conducted with a three field treatment technique using 15 MV X-rays produced by an Elekta Precise linear accelerator (Elekta AB, UK) equipped with a multileaf collimator (MLC). The proton beam treatment is conducted with a single perineal proton beam individually shaped with an aperture and diverging collimator. The range compensation filters are calculated to obtain a distal dose distribution which conforms to the PTV.

For the purpose of comparative treatment planning, two different proton beam treatment plans (i.e. with (proton_with) and without (proton_without) the rectal rod) are compared alone, without combining with X-ray treatments. The maximum dose and the volume receiving at least 63% of the normalization dose (this dose level will correspond to approximately 70 Gy when the proton plan is combined with the X-ray treatment) to the two different definitions of the rectum volume is compared for the two proton beam treatment plans (both plans are covering the whole planning target volume with at least 95% of the normalization dose).

Dose distributions in a transverse and a sagittal section in the central part of the prostate for one representative patient are shown in FIGS. 3a-3d for the two different treatment plans. The absolute volume of the two rectum volumes receiving 63% or more of the prescribed doses are given in Table I for the ten patients for the two proton beam treatment plans. The maximum dose, in percentage of the normalization, to the two rectum volumes are also presented in Table I.

TABLE I

The absolute volume receiving 63% or more of the prescribed doses and the maximum dose of the two rectum volumes.

| | Plan | | | | | | | |
|---|---|---|---|---|---|---|---|---|
| | Volume Rectum_out (cm³) | | Volume Rectum_in (cm³) | | Maximum dose rectum_out (%) | | Maximum dose rectum_in (%) | |
| Patient | Proton_with | Proton_without | Proton_with | Proton_without | Proton_with | Proton_without | Proton_with | Proton_without |
| 1 | 2.4 | 10.6 | 0 | 6.4 | 94.5 | 99.2 | 33.6 | 98.9 |
| 2 | 0 | 9.1 | 0 | 3 | 89.1 | 99.8 | 40.8 | 97.3 |
| 3 | 0.4 | 5.8 | 0 | 5.1 | 80.0 | 99.3 | 48.6 | 97.1 |
| 4 | 0.3 | 1.9 | 0 | 0.3 | 70.3 | 92.2 | 39.1 | 70.7 |
| 5 | 4.2 | 7.8 | 0.8 | 3.6 | 95.8 | 99.6 | 83.3 | 97.1 |
| 6 | 1.9 | 9.0 | 0 | 4.5 | 95.7 | 100.5 | 59.5 | 100.4 |
| 7 | 5.0 | 7.6 | 0.7 | 2.5 | 94.2 | 99.1 | 73.3 | 94.8 |
| 8 | 0.7 | 19.5 | 0 | 3.1 | 81.6 | 100.8 | 48.9 | 97.5 |
| 9 | 0.6 | 7.5 | 0 | 3.1 | 74.6 | 99.3 | 62.5 | 98.4 |
| 10 | 3.4 | 4.9 | 0.4 | 2.2 | 96.6 | 98.7 | 67.8 | 95.6 |
| mean | 1.9 | 8.4 | 0.2 | 3.4 | 87.2 | 98.8 | 55.7 | 94.8 |

Both treatment plans cover the PTV well, as the target coverage is 100% for all ten patients for both plans. The treatment plan with the rectal rod reduces significantly (p<0.01) the volume receiving 63% or more of the prescribed dose to both defined rectum volumes for all patients. In mean, the reduction is 77% and 94% for the rectum_out and the retum_in volume, respectively. The maximum dose to the two rectum volumes was significantly (p<0.01) lower for the treatment plan with rectal rod. In mean, the reduction is 12% and 41% for the rectum_out and the rectum_in volume, respectively.

According to the described embodiment of the method, the volume of the rectum receiving high doses when treating prostate cancer patients with proton beam radiotherapy is reduced. In this example, the volume receiving 70 Gy or more with a combined proton and X-ray treatment is significantly reduced.

The therapeutic advantage for hypofractionation for the treatment of localized prostate cancer has been discussed extensively and recently, there has been significant interest in pursuing hypofractionated schedules with external radiation therapy. However, an obvious concern with high-dose hypofractionated schedules is not prostate cancer cell kill, but rather the potential higher rates of late radiation toxicities. By limiting the rectal volume receiving 70 Gy to less than 10 ml, the associated risk of Grade 2 or 3 rectal complications is lowered.

The present example describes the inventive method using proton beam treatments; however, the present method also can be used in other radiotherapy treatments and may be used with an increased fraction dose and a shortened treatment time with lower or conserved late rectal complication rates. In addition to possible radiobiologic gains, there are other obvious benefits to a hypofractionated treatment regime. The shorter time scale for treatment delivery and reduced numbers of delivered fractions lead to markedly improved patient convenience and substantial savings in resources. The present method can also be used for other therapies where an increased distance between the target organ and the rectum is desired The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A method for radiotherapy treatment of a target organ in the vicinity of the rectum in an individual, comprising withdrawing the rectum in a dorsal direction by insertion of a cylindrically shaped rectal rod into the rectum and withdrawal of the rectum therewith to increase a distance between the rectum and the target organ, and administering a therapeutical dose of radiation to the target organ while the rectum is in the withdrawn position.

2. The method of claim 1, wherein the rod and a beam of the administered radiation are substantially parallel.

3. The method of claim 1, wherein the radiation comprises proton beam radiation.

4. The method of claim 3, wherein X-ray radiation is also administered to the target organ.

5. The method of claim 3, wherein the proton beam radiation is administered in successive doses.

6. The method of claim 1, wherein the radiation comprises X-ray beam radiation.

7. The method of claim 6, wherein the X-ray beam radiation is administered in successive doses.

8. The method of claim 1, wherein the target organ comprises the prostate.

9. The method of claim 8, wherein the prostate is maintained in substantially one position during the administration of radiation to the prostate.

10. The method of claim 9, wherein the prostate is maintained in substantially one position by the rectal rod during the administration of radiation to the prostate.

11. The method of claim 1, wherein at least one detectable marker is applied to the target organ to allow detection of the target organ position during administration of radiation.

12. The method of claim 11, wherein markers are applied to provide three dimensional localization of the target organ position during administration of radiation.

13. The method of claim 1, wherein the radiation comprises proton beam radiation and the rectal volume receiving 70 Gy or more of proton beam radiation is less than 5 ml.

14. The method of claim 1, wherein the radiation comprises proton beam radiation and the rectal volume receiving 70 Gy or more of radiation is at least 50% less than the rectal volume receiving 70 Gy or more of radiation in a similar method wherein the rectum is not withdrawn.

15. The method of claim 14, wherein the rectal volume receiving 70 Gy or more of radiation is at least 70% less than the rectal volume receiving 70 Gy or more of radiation in a similar method wherein the rectum is not withdrawn.

16. The method of claim 1, wherein the cylindrical rectal rod is non-imaging.

17. A system for use in radiotherapy treatment with a radiation source, for treatment of a target organ in the vicinity of the rectum, in an individual, comprising a means for withdrawing the rectum comprising a non-imaging cylindrical rectal rod adapted for insertion into the rectum of the individual, wherein the cylindrical rectal rod is cylindrical along its entire length and has a free distal end for insertion into a rectum, and a support surface operable to support an individual in a lithotomy position to receive a beam of radiation to the target organ.

18. The system of claim 17, further comprising a radiation source for administering a beam of radiation to a prostate of an individual.

19. The system of claim 17, wherein the support surface comprises a fixation couch.

20. The system of claim 17, further comprising a support for an individual's legs.

21. The system of claim 17, further comprising a perineum plate operable to standardize a distance from the skin of an individual to the target organ of an individual.

22. The system of claim 17, wherein the radiation source comprises a proton beam source.

23. The system of claim 17, wherein the cylindrical rectal rod is formed of polymethylmethacrylate.

24. The system of claim 17, further comprising at least one detectable marker adapted for application to a target organ to allow detection of the target organ position during administration of radiation.

25. The system of claim 17, wherein the cylindrical rectal rod has a length of from about 20 cm to about 30 cm and a diameter of from about 1 cm to about 3 cm.

* * * * *

UNITED STATES PATENT AND TRADEMARK OFFICE
CERTIFICATE OF CORRECTION

PATENT NO. : 7,771,339 B2  Page 1 of 1
APPLICATION NO. : 11/807951
DATED : August 10, 2010
INVENTOR(S) : Ulf Isacsson et al.

It is certified that error appears in the above-identified patent and that said Letters Patent is hereby corrected as shown below:

Title Page in field (75) Inventors, change "Jaerlassa" to --Jaerlaasa--.

Signed and Sealed this

Twelfth Day of October, 2010

David J. Kappos
*Director of the United States Patent and Trademark Office*